(12) United States Patent
Busch et al.

(10) Patent No.: US 8,808,289 B2
(45) Date of Patent: Aug. 19, 2014

(54) COUPLING ELEMENT FOR AN EXTERNAL FIXATOR

(75) Inventors: Adam Busch, Olten (CH); Vadim Gurevich, West New York, NJ (US); Klaus Dorawa, Safnern (CH)

(73) Assignee: Stryker Trauma SA (CH)

( * ) Notice: Subject to any disclaimer, the term of this patent is extended or adjusted under 35 U.S.C. 154(b) by 237 days.

(21) Appl. No.: 13/240,221

(22) Filed: Sep. 22, 2011

(65) Prior Publication Data

US 2012/0093575 A1  Apr. 19, 2012

(30) Foreign Application Priority Data

Oct. 7, 2010  (EP) .................................... 10186847

(51) Int. Cl.
*A61B 17/60* (2006.01)

(52) U.S. Cl.
USPC ............................... 606/54; 606/324; 403/72

(58) Field of Classification Search
USPC .................. 403/72, 73, 76, 78, 164; 606/324, 606/54–59
See application file for complete search history.

(56) References Cited

U.S. PATENT DOCUMENTS

| | | | |
|---|---|---|---|
| D255,713 S | 7/1980 | Sturges | |
| 5,160,335 A | 11/1992 | Wagenknecht | |
| 5,304,177 A | 4/1994 | Pennig | |
| 5,358,504 A | 10/1994 | Paley et al. | |
| 5,376,091 A | 12/1994 | Hotchkiss et al. | |
| 5,443,465 A | 8/1995 | Pennig | |
| 5,662,651 A | 9/1997 | Tornier et al. | |
| 5,752,954 A | 5/1998 | Mata et al. | |
| 5,846,245 A | 12/1998 | McCarthy et al. | |
| 5,891,144 A | 4/1999 | Mata et al. | |
| 6,019,769 A | 2/2000 | McCarthy et al. | |
| 6,080,153 A | 6/2000 | Mata et al. | |
| D455,831 S | 4/2002 | Koros et al. | |
| 6,409,729 B1 | 6/2002 | Martinelli et al. | |
| 6,520,962 B1 | 2/2003 | Taylor et al. | |
| 6,702,814 B2 | 3/2004 | Walulik et al. | |
| 6,872,209 B2 | 3/2005 | Morrison | |

(Continued)

FOREIGN PATENT DOCUMENTS

| | | |
|---|---|---|
| EP | 0700664 A1 | 3/1996 |
| WO | 0247564 A2 | 6/2002 |

OTHER PUBLICATIONS

European Search Report EP 09170102, dated Feb. 18, 2010.
European Search Report EP 10186847.9 dated Jan. 31, 2011.

(Continued)

*Primary Examiner* — Eduardo C. Robert
*Assistant Examiner* — Julianna N Harvey
(74) *Attorney, Agent, or Firm* — Lerner, David, Littenberg, Krumholz & Mentlik, LLP (57) ABSTRACT

Coupling element for an external fixator which connects a pin or rod to a second pin or rod. The coupling element comprises a first coupling section to clamp the first pin or rod in engagement with a second clamp for clamping the second pin or rod and a pivoting section for adjusting the orientation of the first coupling section relative to the post section in the space. The pivoting section extends along a third axis. The first coupling section is rotatable around a first axis with respect to the pivoting section and wherein via the pivoting section the first coupling section is pivotable around a second axis with respect to the post section, wherein the second axis is arranged at an angle to the first axis.

14 Claims, 6 Drawing Sheets

(56) References Cited

U.S. PATENT DOCUMENTS

| | | |
|---|---|---|
| 7,004,943 B2 | 2/2006 | Ferrante et al. |
| 7,048,735 B2 | 5/2006 | Ferrante et al. |
| D526,410 S | 8/2006 | Phillips et al. |
| D537,939 S | 3/2007 | Phillips et al. |
| 7,241,074 B2 | 7/2007 | Thomke et al. |
| 7,261,713 B2 | 8/2007 | Langmaid et al. |
| D551,763 S | 9/2007 | Phillips et al. |
| 7,282,052 B2 | 10/2007 | Mullaney |
| 7,479,142 B2 | 1/2009 | Weiner et al. |
| 7,562,855 B2 | 7/2009 | Oetlinger |
| 7,578,822 B2 | 8/2009 | Rezach et al. |
| 8,029,505 B2 | 10/2011 | Hearn et al. |
| 2001/0049526 A1 | 12/2001 | Venturini et al. |
| 2002/0077629 A1 | 6/2002 | Hoffman et al. |
| 2003/0187432 A1 | 10/2003 | Johnson et al. |
| 2003/0199738 A1 | 10/2003 | Yager |
| 2004/0044344 A1 | 3/2004 | Winquist et al. |
| 2004/0059331 A1 | 3/2004 | Mullaney |
| 2004/0158245 A1 | 8/2004 | Chin |
| 2004/0249375 A1 | 12/2004 | Agee et al. |
| 2005/0113829 A1 | 5/2005 | Walulik et al. |
| 2005/0119656 A1 | 6/2005 | Ferrante et al. |
| 2005/0240265 A1 | 10/2005 | Kuiper et al. |
| 2006/0025703 A1 | 2/2006 | Miles et al. |
| 2006/0039750 A1 | 2/2006 | Thomke et al. |
| 2006/0052781 A1 | 3/2006 | Thomke et al. |
| 2006/0052785 A1 | 3/2006 | Augostino et al. |
| 2006/0155276 A1* | 7/2006 | Walulik et al. .............. 606/59 |
| 2006/0167453 A1 | 7/2006 | Hoffmann-Clair et al. |
| 2006/0229604 A1 | 10/2006 | Olsen et al. |
| 2007/0123856 A1 | 5/2007 | Deffenbaugh et al. |
| 2008/0188852 A1 | 8/2008 | Matityahu |
| 2008/0215053 A1 | 9/2008 | Thomke et al. |
| 2008/0294198 A1 | 11/2008 | Jackson |
| 2008/0306527 A1 | 12/2008 | Winslow et al. |
| 2009/0018541 A1 | 1/2009 | Lavi |
| 2009/0088751 A1 | 4/2009 | Mullaney |
| 2009/0099565 A1 | 4/2009 | Weiner et al. |
| 2009/0228006 A1 | 9/2009 | Mussolin |
| 2009/0287212 A1 | 11/2009 | Hirata et al. |
| 2011/0061151 A1 | 3/2011 | Chang |

OTHER PUBLICATIONS

Kinbrum "The PEEK of Large Joint Performance?", Orthopedic Design & Technology, pp. 51-55, Mar./Apr. 2009.

\* cited by examiner

COUPLING ELEMENT FOR AN EXTERNAL FIXATOR

CROSS-REFERENCE TO RELATED APPLICATION

The present application claims priority from European Patent Application No. EP 10 186 847.9 filed Oct. 7, 2010, which is incorporated herein by reference.

BACKGROUND OF THE INVENTION

The present invention relates to a coupling element for an external fixator and to an external fixation system using the coupling system.

From prior art there are many systems known to treat fractures and/or to make post operative corrections with regard to bone fractures. For example there is a system under name "Hoffmann II compact—External Fixation System" known from the applicant. With this system the surgeon as well as the patient were very pleased as it allows very good bone correction is advantageous for the healing process. However, due to increasing cost in the health sector there is a general need to shorten the period to apply such a system even more.

Further systems are also known, but the application of some of them is rather cumbersome due to the use of many different elements. The presence of many elements is a drawback, since the surgeon has to adjust all of them and uses several supporting persons in order to apply the system correctly. This leads to increased time in the operating room.

A coupling element is shown in U.S. Patent Application Publication No. 2011/0066151 the disclosure of which is incorporated herein by reference. This publication is assigned to the assignee of the present invention.

BRIEF SUMMARY OF THE INVENTION

It is therefore one aspect of the present invention to provide a coupling element to be used in an external fixator which overcomes the problems of prior art. In particular such a coupling element can be applied in a faster manner in order to save valuable time and therefore to reduce costs.

Such an aspect is solved by a coupling element for an external fixator arrangement to connect a pin clamp that clamps at least one pin or a rod with a further rod. This coupling element comprises a rod coupling section to clamp the rod wherein the coupling element further comprises a post section to be in an engagement via the pin clamp with the pin and a pivoting section to adjust the orientation of the rod coupling section relative to the post section in the space. The rod coupling section is rotatable around a first axis with respect to the pivoting section and wherein via the pivoting section the rod coupling section is pivotable around a second axis with respect to the post section, wherein the second axis is arranged at an angle to the first axis.

Due to the arrangement of the post section such a coupling element can be directly connected to the pin clamp which saves time during surgery. Preferably the pivoting section is rotatable around a third axis with respect to the post section. This allows more freedom in adjusting the device.

The first axis is preferably substantially perpendicular to the second axis and/or the third axis is preferably substantially perpendicular to the second axis. This provides the user with a device that has good reference positions enabling easy manipulation.

Preferably the pivoting section is in connection by means of a first joint with the coupling section and by means of a second joint with the post section which joints permit the rotation around the first axis or the third axis.

Preferably a first tightening element is used to block rotation of the rod coupling section around the first axis and to block pivot-motion of the rod coupling section with respect to the pivoting section around the second axis and wherein with the first tightening element a rod which is in connection with the rod coupling section will be fixed to the coupling element.

Preferably a second tightening element is used to block rotation of the pivoting section around the third axis and to block pivot-motion of the post section with respect to the pivoting section around the second axis.

Preferably the second tightening element comprises a screw and two wedge elements which are moveable against each other, wherein said wedge elements are in contact with a sloped flange of the post section, whereby upon actuation of the screw the wedge elements move together and, due to sloped flange, towards the plate in order to block the rotation of the pivoting section and pivot-motion of the post section. The wedge elements can alternatively or additionally also be in contact with a sloped surface that is arranged on the second joint. The main function of said wedge elements and the corresponding sloped surfaces is to provide an axial clamping force which clamps the respective elements so that the second joint and the lower part of the pivoting section or pivoting joint that is contact with the second joint can be locked or fixed with respect to the post section.

A coupling element for an external fixator comprising: a first rod clamping section including upper and lower jaw members rotatably mounted on a first shaft extending along a first axis. A post section is provided which has a second shaft extending along a second axis. The post section includes a flange extending at an angle to the second axis. A pivot section is provided having a cylindrical surface extending about a third axis in a direction perpendicular to first and second axes. First and second locking elements are respectively mounted on the first and second shafts capable of engaging a cylindrical locking surface on the pivot section. First and second wedge elements are moveably mounted on the post section second shaft. The wedge elements include a sloped surface for engaging a sloped surface of the flange. The wedge elements are moveable toward the second axis for locking the second locking element on the cylindrical locking surfaces of the pivot section. The first shaft comprises a threaded bolt extending through a bore in the upper and lower jaws and having the first locking element threaded on an end of the bolt. The wedge elements move in a direction perpendicular to the second axis by the action of a threaded bolt threaded into one of the wedge elements. The coupling element comprises a pin or rod clamp coupled to the post section.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DETAILED DESCRIPTION

Figure 4:
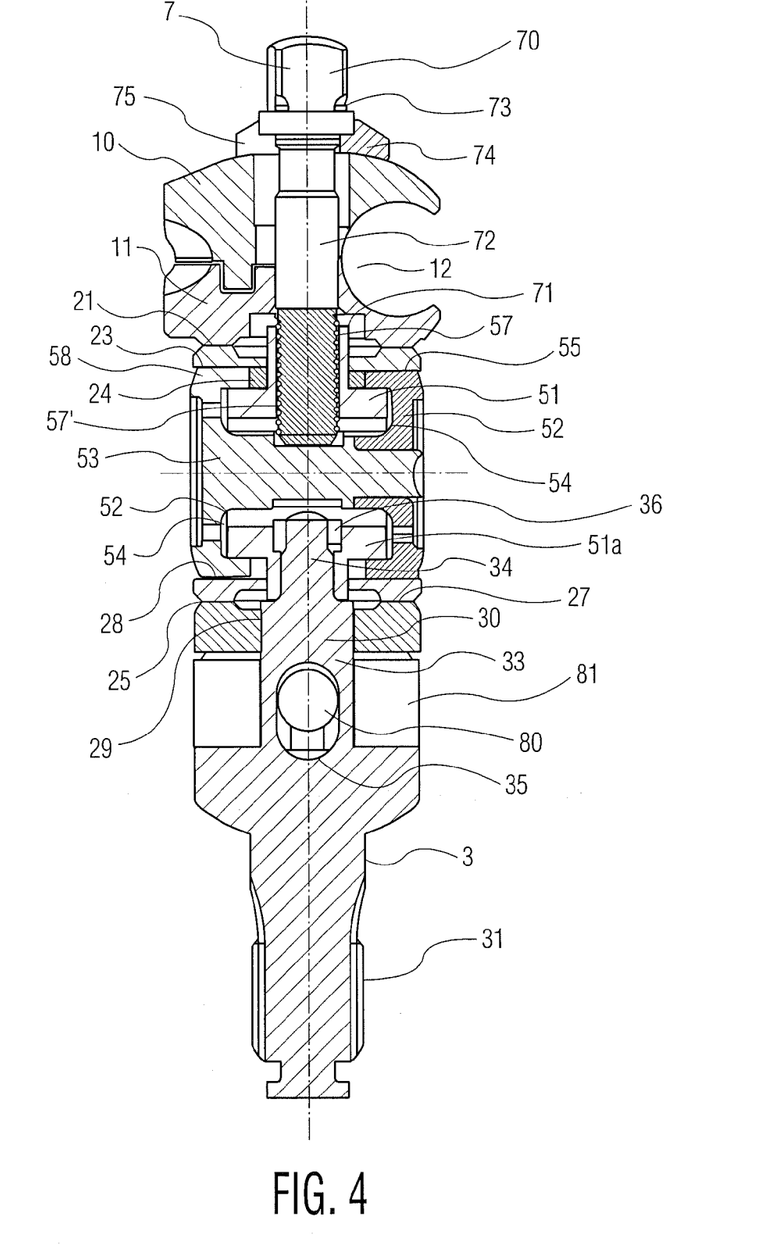
FIG. 4 shows a cross-sectional view along lines 4-4 of the coupling element according to FIG. 1.
Figure 5:
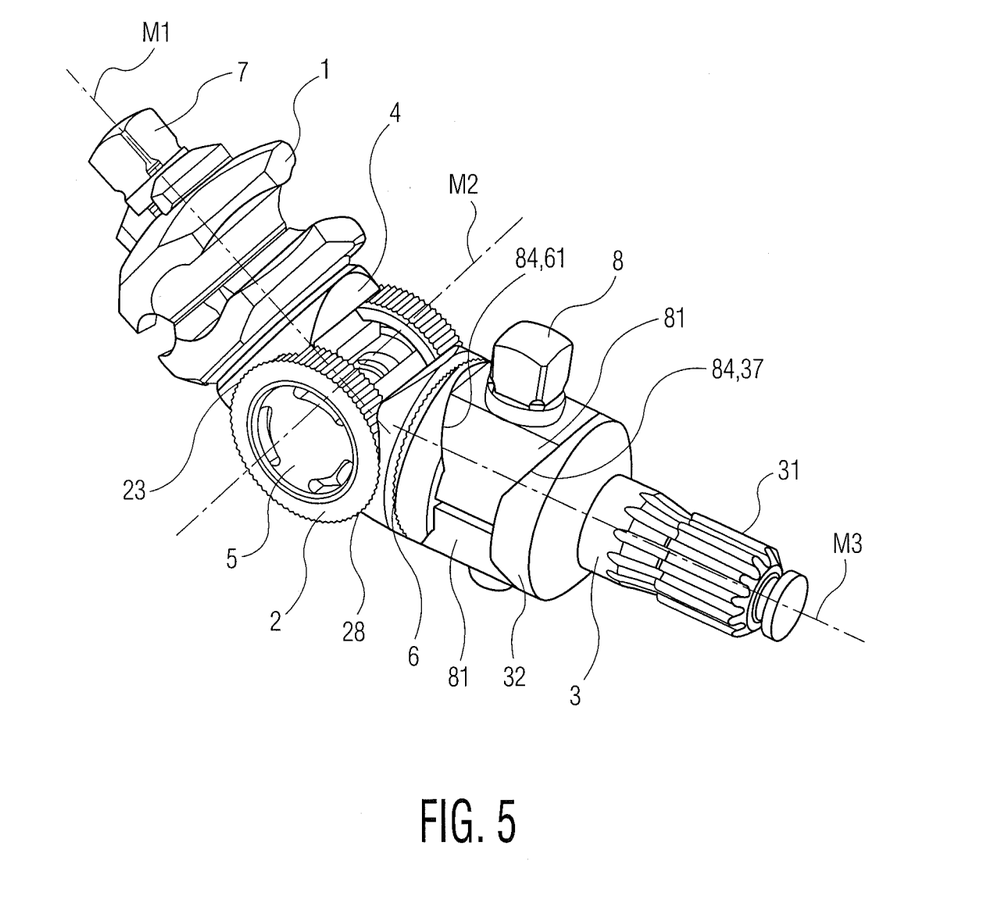
FIG. 5 shows a perspective view of the coupling element according to FIGS. 1 to 4.
Figure 6:
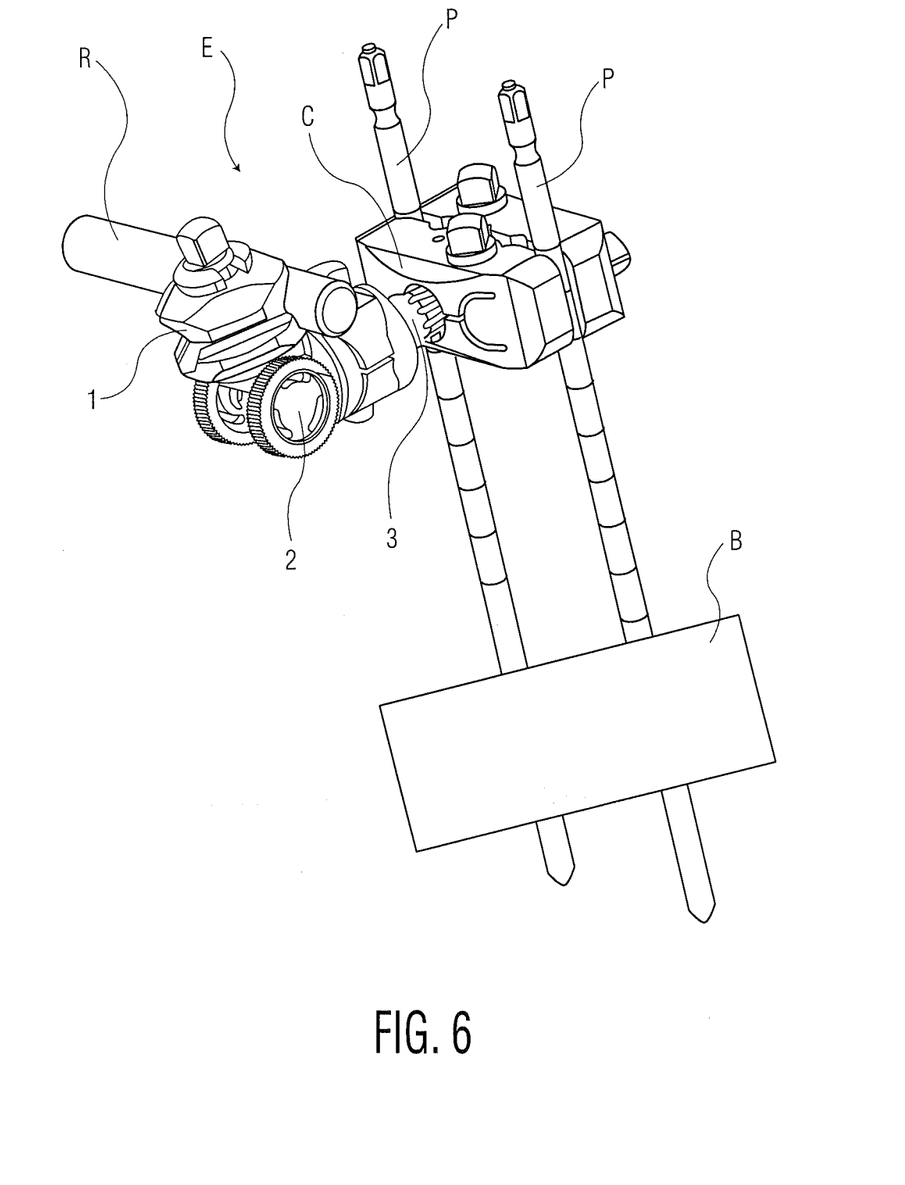
FIG. 6 shows a perspective of an external fixator system in which a coupling according to the previous figures is used.

In FIGS. 1 to 5 there is shown a coupling element E for use in an external fixator arrangement to correct a bone fracture and/or to make post-operative corrections. FIG. 6 shows the external fixator comprising a plurality of pins P which are in contact with bony structure B, pin clamp C which clamps pins P, coupling element E connects the pin clamp C with a rod R or several rods via rod coupling section 1. Therefore the coupling element E is in contact with the pin clamp C and with the rod R which itself is moveable in contact with a further coupling element E that connects the rod to further pin(s) P (now shown).

Coupling element E comprises a rod coupling section 1, a pivoting section 2, and a post section 3. The pivoting section 2 is arranged between the rod coupling section 1 and the post section 3. The rod coupling section 1 serves to clamp or couple one of said rod(s) R to the coupling element E. The pivoting section 2 serves to adjust the orientation of rod coupling section 1 relative to post section 3 in the operation space of coupling element E. The post section 3 is in a fixed engagement/contact with pin clamp C which clamps the pins P.

The rod coupling section 1 is rotatable around a first axis M1 with respect to the pivoting section 2. Thereby permitting positioning of rod coupling section 1 around an axis of rotation relative to pivoting section 2. With regard to the post section 3 which may serve as a fixed reference in the operation space this also means that the rod coupling section 1 is rotatable.

The arrangement of the pivoting section 2 allows that the rod coupling is pivotable around a second axis M2 with respect of said post section 3. The second axis M2 is thereby arranged at an angle to the first axis M1. Preferably the second axis M2 is at 90° (perpendicular) with respect to the first axis M1.

The pivoting section 2 itself is furthermore rotatable around a third axis M3 with respect to said post section. The third axis M3 is also arranged at an angle to the second axis M2, preferably a 90° angle (perpendicular). Thereby enabling further adjustments of the orientation.

Figure 1:
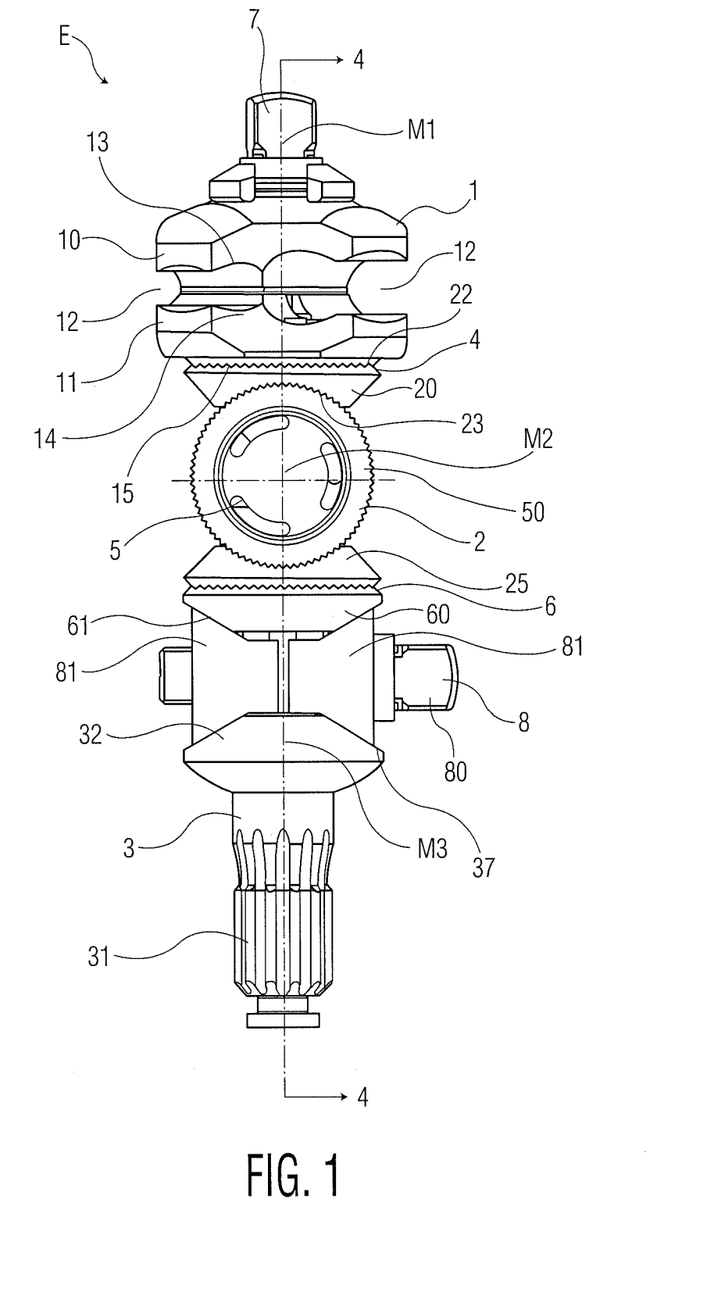
FIG. 1 shows an elevation view of a coupling element for use in an external fixator arrangement to connect a pin clamp that clamps at least one pin with a rod.
Figure 2:
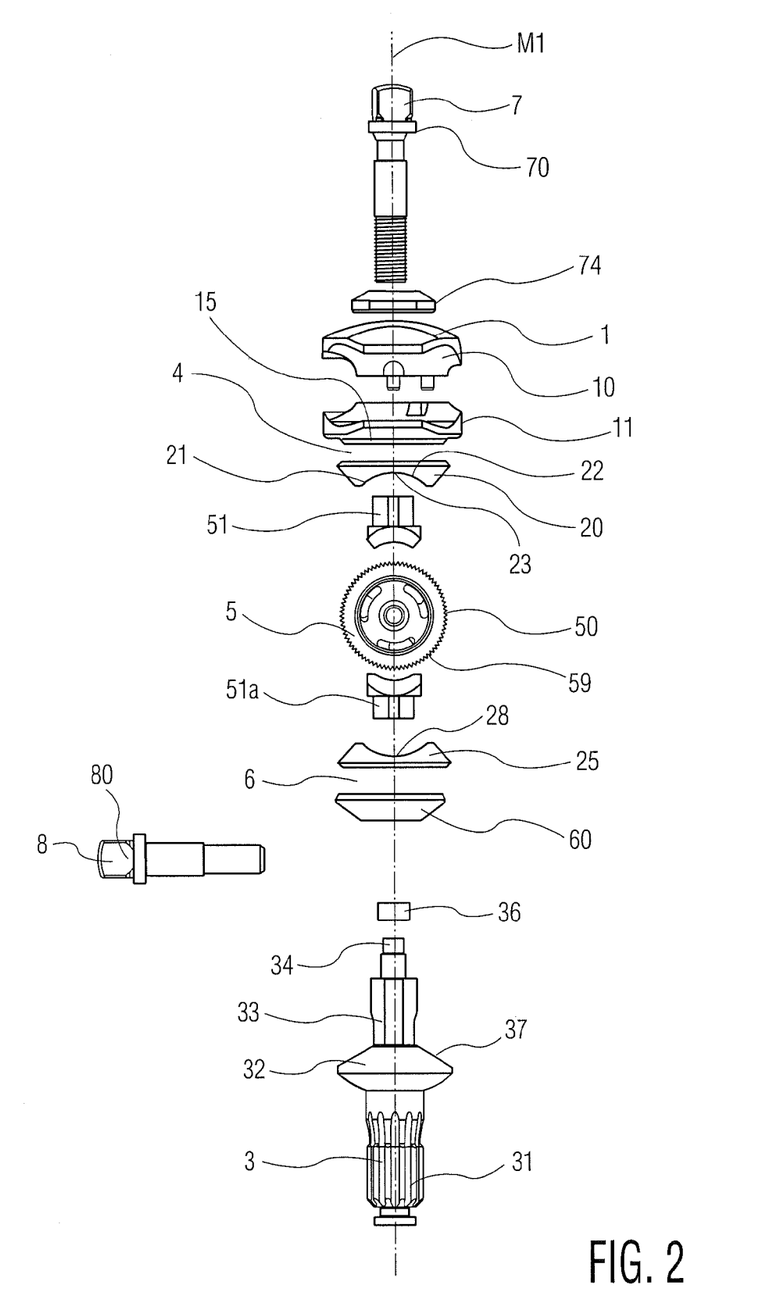
FIG. 2 shows an exploded view of the coupling element according to FIG. 1.

With such a configuration it is possible to orient the rod coupling section 1 with respect to the post section 3 completely in its operation space. This means that the rod coupling section 1 is rotatable around the third axis M3, pivotable around the second axis M2 which is angular, preferably perpendicular, to said middle axis M3 and rotatable around the first axis M1. Thereby rod coupling section 1 can be rotated in all degree of freedoms as viewed from the virtually fixed post section 3. In FIG. 1 the first axis M1 and the third axis M3 are shown collinear. Due to the arrangement of the second axis M2 which is angular, e.g. perpendicular, to the first axis M1 and to the third axis M3, said rod coupling section 2 can be pivoted to the post section 3 so that the first axis M1 and the third axis M3 are arranged angular to each other. Such a pivoted position is shown in FIGS. 5 and 6.

With regard to FIGS. 1 to 4 the mechanical construction of the embodiment as shown will now be explained.

The rod clamping section 1 extends along the first axis M1. The rod clamping section 1 comprises a first jaw 10 and a second jaw 11 both of which define at least one clamping opening 12 with which a rod R can be clamped. Thereby the clamping opening 12 is provided by respective channels 13, 14 that are arranged in the first jaw 10 and in the second jaw 11. In the present embodiment there are three clamping openings 12 arranged which serve to clamp rods with three different diameters. The clamping openings 12 extend along an axis which is angular, preferably perpendicular, to the first axis M1. For example the clamp is shown in U.S. Patent Application Publication No. 2010/0298827, the disclosure of which is incorporated herein by reference, may be used.

The rod clamping section 1 is in connection with the pivoting section 2 by means of a first joint 4. In the present embodiment the first joint 4 is provided by means of the second jaw 11 and a bearing element 20 of the pivoting section 2. The jaw 11 faces the bearing element 20 by means of a surface 15 and the bearing element 20 faces the jaw 11 by means of a surface 21. Preferably both of the surfaces 15, 21 are provided with a plurality of teeth 22 which are arranged around the middle axis M1 in a ring-shaped manner. Thereby teeth 22 arranged on surface 15 of the jaw 11 engages into the teeth 22 of the surface 21 of the bearing element 20 so that a form closure can be obtained. Alternatively it is also possible to arrange such a plurality of teeth 22 only one of the surfaces. Thereby such a structure serves as friction enhancing structure. In either case relative rotation about axis M1 is prevented.

The pivoting section 2 comprises mainly a pivoting mechanism 5 which allows rod coupling section 1 to pivot around the second axis M2 extending through pivoting mechanism 5. As seen from the fixed post section 3 this means that the rod coupling section 1 is pivotable around second axis M2 and is rotatable around first axis M1.

The pivoting mechanism 5 comprises two bearing elements 20, 25, a pivoting cylinder 50, and first and second fixation elements 51 and 51a. The first bearing element 20 is thereby also part of the first joint 4 as it is mentioned above and the second bearing element 25 is part of the second joint 6 as mentioned below.

Figure 3:
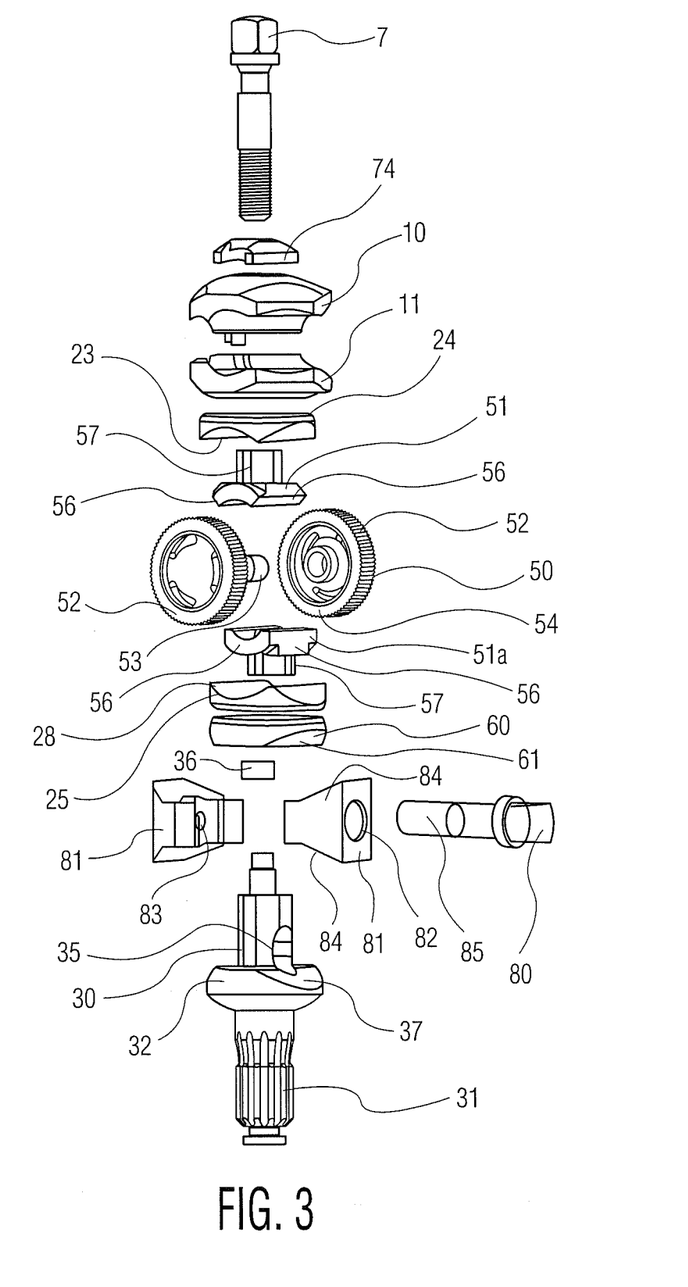
FIG. 3 shows an exploded view of the coupling element according to FIGS. 1 to 2.

The pivoting cylinder 50 extends along the second axis M2 and comprises two flanges 52 and an axle 53 which connects the flanges 52. Thereby the flanges 52 are arranged at a distance to each other. Within the flanges 52 there is arranged a channel 54 which extends around the second axis M2. The channels 54 are arranged to receive parts of the fixation elements 51, 51a. As shown in FIG. 3 it is preferably that one of the flanges 52 and the axle 53 are made out of one single piece. The other flange 52 can be connected to the axle 53 by means of a thread or a press fit. However, it is also possible to connect both of the flanges 52 to the axle 53. The separation of at least one of the flanges 52 is necessary to mount the fixation elements 51, 51a as explained below.

As mentioned above the bearing element 20 comprises a surface 21 facing the rod coupling section 1. Furthermore the bearing element 20 comprises a second surface 23 facing the pivoting mechanism 5 in particular the pivoting cylinder 50. The second surface 23 is concave having the same curvature as the pivoting cylinder 50, so that the pivoting cylinder can be in contact with second surface 23. Furthermore the bearing element 20 comprises a central opening 24 which extends from the surface 21 to the second surface 23 along the first axis M1. The same applies to the bearing element 25 which comprises also surface 26 facing the post section 3, a second surface 28 facing the pivoting mechanism 5 and a central opening 29.

The pivoting cylinder 50 is arranged between the bearing elements 20 and 25 and is in contact with the respective second surface 23, 28. The surfaces 23, 28 which are in contact with flanges 52 are also provided with teeth such that a firm connection can be provided. For clarity only the toothed structure on the flanges 52 have been designated by reference numeral 55. However, it may also be possible to omit the toothed structure.

The fixation elements 51, 51a extend with arms 56 into the channels 54 and is in contact with the same with the axle 53. From arms 56 a boss 57 with a threaded opening 57' extends along axis M1 and M3 respectively. The threaded opening 57' is in contact with a first tightening element 7 which has the shape of a screw 70. The first tightening element 7 or screw 70 extends through the rod coupling section 1 into the pivoting section 2. Upon actuation of the screw 70 the first jaw 10 and the second jaw 11 will be moved towards each other so that a rod can be clamped. Furthermore the bearing element 21 and the pivoting cylinder 50 will also be moved together and will be clamped. In other words: actuation of the screw 70 results in tightening the rod coupling section 1 and the upper part 58 of the pivoting mechanism or the pivoting section 2, respectively.

The fixation elements 51, 51a can be introduced into one of the channels 54. Afterwards the other flange 52 can be mounted so that the fixation elements 51, 51a extend into both flanges 52. This can be seen in FIG. 4.

Once the orientation of the rod coupling section 1 around the middle axis M1 and around the middle axis M2 has been accomplished the screw 70 can be actuated and the rod section 1 as we as the upper part of the pivoting section 2 will be fixed.

The post section 3 is as already mentioned in connection with the pivoting section 2. Thereby the post section 3 is also pivotable around the second axis M3. Furthermore the post section 3 is connected by means a second joint 6. The second joint 6 is provided such that a rotation around the third axis M3 is permitted. In principle the second joint 6 has the same structure as the first joint 4. The second joint 6 comprises a bearing element 25 which is in connection with the pivoting cylinder 50 and a further plate 60 is arranged below the bearing element 25. Plate 60 serves to block rotation of the second joint 6. Bearing element 25 and plate 60 may also be provided with a friction enhancing structure (teeth) as mentioned with regard to the first joint 4.

The post section 3 further comprises a second tightening element 8 which is used to fixate the second joint 6 as well as the lower part 59 of pivoting mechanism 5. The tightening element 8 comprises a screw 80 and two wedge elements 81 which are moveable against each other. Each of the wedge elements 81 have at least one sloped surface 84 which extends at an angle to the middle axis M3. In the present embodiment each of the wedge elements have two sloped surfaces 84. Thereby the wedge elements 81 are in contact via the sloped surface 84 with a sloped surface 37 on a flange 32 of the post section 3 and with a sloped flange 61 on plate 60. The screw 80 extends through an opening 82 in one of the wedge elements 81 and is in contact with a threaded opening 83 in the other wedge element 81. Furthermore the screw extends through opening 35 in the post section 3 and the wedge elements 81 enclose post section 3 at least partly. Upon rotation of the screw 80 the two wedge elements 81 will be moved against each other and due to the sloped flanges 84 which are in contact with the sloped surfaces 37 and 61 the wedge elements 81 will move the plate 60 against the bearing element 25. Therefore an axial force in direction of the third axis M3 is exerted by means of the wedge elements 81 towards the post 30 and bearing plate 25 which is in connection with the post 30 by means of the fixation element 51 as it is explained below. Thereby the joint 6 and the lower part 59 of the pivoting mechanism 5 (i.e. the connection between the pivot section 2 and the post 3) will be locked or fixed by said axial force exerted upon tightening of the wedge elements 81. This means that rotation of the pivot section 2 around the second axis M2 and the third axis M3 relative to the post section 3 will be prevented.

The post section 3 comprises post 30 which extends substantially along the third axis M3 and comprises a spline section 31, flange 32, a bearing section 33 and connection element 34. The opening 35 as mentioned above is arranged within the bearing section 33. The spline section 31 serves as connection element to connect the whole coupling element to a clamping element for example pin clamp C. Due to the arrangement of the splines 31 the user may orient the coupling element approximately. The fine orientation can then be made by the joints 5 and 6. The bearing section 32 is arranged to guide the wedge elements 81, the screw 80 and the plate 60 as well as the plate 25. The post 30 is in connection with the second fixation element 51a by means of a ring element 36 which clamps post 30 within the second fixation element 51a. The ring element 36 can be connected to the post 30 by means of a press-fit or a threaded structure. From FIG. 4 the connection between the post 30 and the fixation element 51a becomes clear. The post 30 comprises a connection element 34 which can be pressed thorough the opening 57' in the fixation element. In this case the thread within opening 57' can be omitted.

With regard to FIG. 4 the arrangement of the first tightening element 7 will now be explained in greater detail. The first tightening element 7 has the shape of a screw 70 extending along the first axis M1 and comprising a threaded section 71, a shaft section 72 and a head section 73. The head section 73 is adapted to be actuated by a tool. The threaded section 71 is in engagement with the threaded opening 57' in boss 57 of fixation element 51, whereas the shaft section 72 guides the first jaw 10 and the second jaw 11. The head section 73 is contact with the first jaw 10 by means the a disc 74 via which the head section 73 acts on the first jaw 10 and the second jaw 11. Upon actuation of the screw 70 a force will be provided which acts on the jaws 10, 11, on the first joint 5 and on the pivoting mechanism 5. Furthermore the first jaw 10 and the second jaw 11 will be actuated by means of compression spring which is not shown, so that both jaws 10, 11 will be pressed against the disc 74. The disc 74 itself comprises a slot 75 so that the disc 74 can be mounted after the screw 70 secures the jaws 10, 11. Furthermore there is optionally a spring arranged which pushes the first jaw 10 apart from the second jaw 11 such that the user is able to introduce a rod R in a very easily manner.

FIG. 5 shows the coupling element whereby the rod coupling section 1 is pivoted around the pivoting section 2 or the second axis M3 respectively, with regard to the post section 3.

FIG. 6 shows an external fixation system with a coupling element E as described herein. The external fixator system comprises a plurality of pins P, a pin clamp C, the coupling element E as well as a rod R. In the present embodiment the pins P are arranged as pin pairs and extend into bony structure B. Each of the pairs are in connection with a respective pin clamp C. The pin clamps C are then in connection via the post section 3 with the rod coupling element E. Thereby one coupling element E is arranged per pin clamp C. The coupling element E clamps further the rod R with the rod clamping section 1. Thereby the two pin pairs are in connection with each other via the R, the coupling elements E and the pin clamps C.

The invention claimed is:

1. A coupling element for an external fixator arrangement for connecting a pin clamp that clamps at least one pin or a rod with a rod, comprising:
   a rod coupling section for clamping a rod,
   a post section coupled to said pin clamp and
   a pivoting section to adjust the orientation of the rod coupling section relative to the post section,
   wherein the rod coupling section is rotatable around a first axis with respect to the pivoting section and wherein via the pivoting section the rod coupling section is pivotable around a second axis with respect to said post section, wherein the second axis is arranged at an angle to the first axis,
   wherein the pivoting section is rotatable around a third axis with respect to said post section;
   wherein the third axis is substantially perpendicular to the second axis;
   wherein said coupling element comprises a second tightening element that is used to block rotation of the pivoting section around the third axis and to block pivot-motion of the post section with respect to the pivoting section around the second axis; and
   wherein said the second tightening element comprises a screw and two wedge elements having sloped surface which wedges elements are moveable against each other, wherein said wedge elements are in contact with at least one sloped flange of the post section and/or of the pivot section, in particular of a joint, whereby upon actuation of the screw the wedge elements move together and due to the sloped surface and the sloped flange an axial force is provided with which the rotation of the pivoting section and pivot-motion of the post section is blocked.

2. The coupling element according to claim 1, wherein the first axis is substantially perpendicular to the second axis.

3. The coupling element according to claim 1, wherein said coupling element comprises a first tightening element that is used to block rotation of the rod coupling section around the first axis and to block pivot-motion of the rod coupling section with respect to the pivoting section around the second axis and wherein with the first tightening element a rod which is in connection with the rod coupling section will be fixed to the coupling element.

4. The coupling element according to claim 1, wherein the rod coupling section comprises a first jaw and a second jaw which provide at least one clamping opening to clamp said rod, and wherein the second jaw has a contact surface engaging a bearing element which engages the pivoting section.

5. The coupling element according to claim 4, wherein the pivoting section comprises a pivoting mechanism having a pivoting cylinder which is in contact with the bearing element, wherein the bearing element comprises a curved surface which is in contact with said pivoting cylinder, wherein at last one of the curved surface and the said pivoting cylinder comprises optionally a friction enhancing structure.

6. The coupling element according to claim 5, wherein the pivoting section comprises a first fixation element which is in contact with a first tightening element and the rod coupling section and a second fixation element which is in contact with the post section.

7. The coupling element according to claim 6, wherein first and second said fixation elements comprise arms and wherein the pivoting cylinder comprises flanges having channels extending into said flanges, wherein said arms extend into said channels.

8. The coupling element according to claim 1, wherein the pivoting section is in connection by means of a first joint with the coupling section and by means of a second joint with the post section which joints permit said rotation around the first axis or the third axis.

9. The coupling element according to claim 8, wherein said first and second joints are provided by means of a bearing element which is part of the pivoting section and a corresponding element which is part of the rod coupling section or the post section, wherein the bearing element and the corresponding element are in contact via respective surfaces, which surfaces comprises optionally a friction enhancing structure.

10. A coupling element for an external fixation system, comprising:
    a rod coupling section for clamping a rod, the rod coupling section rotatable about a first axis;
    a post section extending along a second axis coupled to a pin clamp that clamps at least one pin; and
    a pivoting section coupled to the post section and the rod coupling section to adjust the orientation of the rod coupling section and post section in space about a third axis, wherein the rod coupling section and post section are rotatable about the third axis to vary the angle between the first and second axis,
    wherein the coupling element further comprises a first means for simultaneously blocking the rotation of the rod coupling section about the first and third axis and a second means for simultaneously blocking the rotation of the post section about the second and third axis; and
    wherein the first blocking means is a threaded locking bolt extending through a bore in the rod coupling section along the first axis and into a threaded bore coupled to the pivot section and wherein the second blocking means comprises a pair of wedge elements movable in a direction perpendicular to the second axis by a threaded bolt engaging a threaded bore in one of the wedge elements.

11. A coupling element for an external fixator comprising:
    a first rod clamping section including upper and lower jaw members rotatably mounted on a first shaft extending along a first axis;
    a post section having a second shaft extending along a second axis, the post section including a flange extending at an angle to the second axis;
    a pivot section having a cylindrical surface extending about a third axis in a direction perpendicular to the first and second axis;
    first and second locking elements respectively mounted on the first and second shafts capable of engaging a cylindrical locking surface on the pivot section; and
    first and second wedge elements moveably mounted on the post section second shaft, the wedge elements including a sloped surface for engaging a shaped surface of the flange, the wedge elements moveable toward the second axis for locking the second locking element on the cylindrical locking surfaces of the pivot section.

12. The coupling element as set forth in claim 11 wherein the first shaft comprises a threaded bolt extending through a bore in the upper and lower jaws and having the first locking element threaded on an end of the bolt.

13. The coupling element as set forth in claim 11 wherein the wedge elements move in a direction perpendicular to the second axis by the action of a threaded bolt threaded into one of the wedge elements.

14. The coupling element as set forth in claim 11 further comprising a pin or rod clamp coupled to the post section.

* * * * *